United States Patent

Minagawa et al.

(10) Patent No.: US 10,618,996 B2
(45) Date of Patent: Apr. 14, 2020

(54) SURFACE MODIFICATION METHOD

(71) Applicants: SUMITOMO RUBBER INDUSTRIES, LTD., Kobe-shi, Hyogo (JP); YAMAGATA UNIVERSITY, Yamagata-shi, Yamagata (JP)

(72) Inventors: Yasuhisa Minagawa, Kobe (JP); Masaru Tanaka, Yamagata (JP); Takashi Hoshiba, Yamagata (JP); Tomokazu Shibuya, Yamagata (JP)

(73) Assignees: SUMITOMO RUBBER INDUSTRIES, LTD., Kobe-Shi, Hyogo (JP); YAMAGATA UNIVERSITY, Yamagata-Shi, Yamagata (JP)

( * ) Notice: Subject to any disclaimer, the term of this patent is extended or adjusted under 35 U.S.C. 154(b) by 0 days.

(21) Appl. No.: 15/495,370

(22) Filed: Apr. 24, 2017

(65) Prior Publication Data

US 2017/0320990 A1  Nov. 9, 2017

(30) Foreign Application Priority Data

May 9, 2016 (JP) .................................. 2016-093935

(51) Int. Cl.
  *B05D 3/06* (2006.01)
  *C08F 283/02* (2006.01)
  (Continued)

(52) U.S. Cl.
  CPC .......... *C08F 283/02* (2013.01); *A61L 29/085* (2013.01); *A61L 29/14* (2013.01); *B05D 3/065* (2013.01); *C08F 2/48* (2013.01); *C08F 265/06* (2013.01); *C08F 283/14* (2013.01); *C08J 7/123* (2013.01); *C08J 7/18* (2013.01);
  (Continued)

(58) Field of Classification Search
  CPC ............................ C09D 151/003; B05D 3/065
  See application file for complete search history.

(56) References Cited

U.S. PATENT DOCUMENTS

2002/0122872 A1  9/2002 Leukel et al.
2003/0203991 A1  10/2003 Schottman et al.
(Continued)

FOREIGN PATENT DOCUMENTS

EP   3127948 A1   2/2017
EP   3135311 A1   3/2017
(Continued)

*Primary Examiner* — Dah-Wei D. Yuan
*Assistant Examiner* — Kristen A Dagenais-Englehart
(74) *Attorney, Agent, or Firm* — Birch, Stewart, Kolasch & Birch, LLP

(57) ABSTRACT

Provided are methods for surface-modifying a thermoplastic resin which produce surfaces that show not only low adsorption of proteins and cells but also selective adsorption or adhesion of specific cells such as cancer cells, and further have excellent durability. A method for surface-modifying an object made of a thermoplastic resin, the method including: step 1 of forming polymerization initiation points on the surface of the object; and step 2 of radically polymerizing at least a hydrophilic monomer starting from the polymerization initiation points by irradiation with UV light having a wavelength of 300 to 400 nm to form a graft layer having a thickness of 2 to 100 nm on the surface of the object.

14 Claims, 1 Drawing Sheet

(51) Int. Cl.

| | |
|---|---|
| *C08F 2/48* | (2006.01) |
| *C08J 7/18* | (2006.01) |
| *A61L 29/14* | (2006.01) |
| *A61L 29/08* | (2006.01) |
| *C08F 265/06* | (2006.01) |
| *C08F 283/14* | (2006.01) |
| *C08J 7/12* | (2006.01) |
| *C09D 151/00* | (2006.01) |
| *C09D 151/08* | (2006.01) |
| *G01N 33/50* | (2006.01) |
| *B05D 3/04* | (2006.01) |

(52) U.S. Cl.
CPC ....... *C09D 151/003* (2013.01); *C09D 151/08* (2013.01); *G01N 33/5005* (2013.01); *A61L 2400/18* (2013.01); *A61L 2420/02* (2013.01); *B05D 3/0486* (2013.01); *B05D 3/067* (2013.01); *B05D 2201/00* (2013.01); *C08J 2333/12* (2013.01); *C08J 2345/00* (2013.01); *C08J 2351/00* (2013.01); *C08J 2351/08* (2013.01); *C08J 2367/02* (2013.01)

(56) References Cited

U.S. PATENT DOCUMENTS

| | | | |
|---|---|---|---|
| 2005/0159720 A1* | 7/2005 | Gentilcore | A61L 15/24 604/367 |
| 2011/0274940 A1 | 11/2011 | Kyomoto et al. | |
| 2011/0305872 A1 | 12/2011 | Li et al. | |
| 2013/0203883 A1* | 8/2013 | Minagawa | C08F 8/44 522/35 |
| 2014/0128493 A1* | 5/2014 | Minagawa | A63C 5/056 522/35 |
| 2014/0155980 A1* | 6/2014 | Turjman | A61B 17/12031 623/1.12 |
| 2014/0322468 A1* | 10/2014 | Minagawa | C08G 69/48 428/36.8 |
| 2016/0122488 A1 | 5/2016 | Minagawa | |

FOREIGN PATENT DOCUMENTS

| | | |
|---|---|---|
| JP | 2003-513132 | 4/2003 |
| JP | 2005-523981 A | 8/2005 |
| JP | 2010-501028 A | 1/2010 |
| WO | WO 2008/019450 A1 | 2/2008 |
| WO | WO 2014/203668 A1 | 12/2014 |

\* cited by examiner

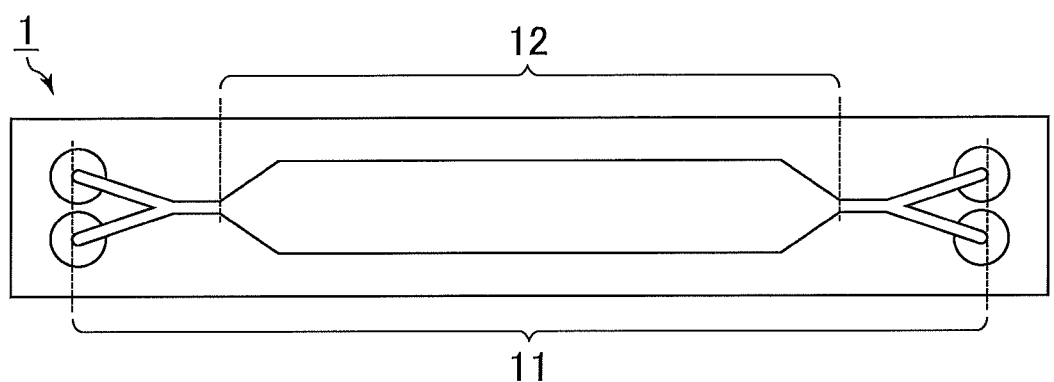

SURFACE MODIFICATION METHOD

TECHNICAL FIELD

The present invention relates to methods for surface modification which produce surfaces that show not only low adsorption of proteins and cells from blood or biological fluid but also selective adsorption or adhesion of specific cells such as cancer cells. The present invention also relates to surface-modified bodies of matrices, filters, channels, tubes, and other devices for medical and healthcare use, at least part of whose surface is modified by the methods.

BACKGROUND ART

Matrices (e.g. substrates, chips, instruments for testing), filters, channels, tubes, and other devices for medical and healthcare use or other uses have a drawback in that since they come into contact with blood or biological fluid inside or outside the body during use, proteins and cells in the blood or biological fluid adhere or adsorb to the surface of the devices and thereby impair the original function of the devices. In order to capture specific cells such as cancer cells for use in diagnosis or treatment, these devices are required to selectively adsorb and collect the specific cells. However, unfortunately, it is also difficult to selectively adsorb them.

Patent Literature 1 proposes to coat the surface of matrices, filters, channels, or tubes for medical and healthcare use with a polymer of a hydrophilic monomer to solve the problems mentioned above. However, this method has a durability problem in that the coating layer may peel or separate due to its hydrophilicity.

CITATION LIST

Patent Literature

Patent Literature 1: JP 2005-523981 T

SUMMARY OF INVENTION

Technical Problem

The present invention aims to solve the aforementioned problems and provide methods for surface-modifying a thermoplastic resin which produce surfaces that show not only low adsorption of proteins and cells but also selective adsorption or adhesion of specific cells such as cancer cells, and further have excellent durability. The present invention also aims to provide surface-modified bodies of matrices, filters, channels, tubes, and other devices for medical and healthcare use, at least part of whose surface is modified by the methods.

Solution to Problem

A first aspect of the present invention relates to a method for surface-modifying an object made of a thermoplastic resin, the method including:
step 1 of forming polymerization initiation points on a surface of the object; and
step 2 of radically polymerizing at least a hydrophilic monomer starting from the polymerization initiation points by irradiation with UV light having a wavelength of 300 to 400 nm to form a graft layer having a thickness of 2 to 100 nm on the surface of the object.

A second aspect of the present invention relates to a method for surface-modifying an object made of a thermoplastic resin, the method including
step I of radically polymerizing at least a hydrophilic monomer by irradiation with UV light having a wavelength of 300 to 400 nm in the presence of a photopolymerization initiator to form a graft layer having a thickness of 2 to 100 nm on a surface of the object.

Step 1 preferably includes adsorbing a photopolymerization initiator to the surface of the object, optionally followed by irradiation with UV light having a wavelength of 300 to 400 nm, to form polymerization initiation points from the photopolymerization initiator on the surface.

The photopolymerization initiator is preferably at least one of a benzophenone compound or a thioxanthone compound.

Preferably, an inert gas is introduced into a reaction vessel or pipe containing a solution of the hydrophilic monomer so that the monomer is radically polymerized in an atmosphere replaced with the inert gas.

The hydrophilic monomer is preferably at least one selected from the group consisting of acrylic acid, acrylic acid esters, methacrylic acid, methacrylic acid esters, acryloylmorpholine, and methacryloylmorpholine.

Preferably, a solution of the hydrophilic monomer containing a polymerization inhibitor is used, and the monomer is radically polymerized in the presence of the polymerization inhibitor.

The thermoplastic resin is preferably at least one selected from the group consisting of acrylic resins, cycloolefin resin, carbonate resin, styrene resin, and polyester resins.

Advantageous Effects of Invention

According to the surface modification methods of the first and second aspects of the present invention, a hydrophilic monomer is radically polymerized to form a thin graft layer having a predetermined thickness (a graft layer formed of hydrophilic polymer chains) on the surface of an object to be modified. As a result, the surface of the object is provided with not only low adsorption properties with respect to proteins and cells in blood or biological fluid, but also selective adsorption or adhesion properties with respect to specific cells such as cancer cells. In addition, since a hydrophilic polymer is fixed on the surface, durability against repeated use is also imparted to the surface so that the deterioration of the low adsorption properties or selective adsorption or adhesion properties can be reduced. Thus, by forming hydrophilic polymer chains (graft layer) with a predetermined thickness on the surface of objects by the methods, it is possible to produce surface-modified bodies of matrices, filters, channels, tubes, and other devices for medical and healthcare use which are excellent in the above properties.

BRIEF DESCRIPTION OF DRAWINGS

FIG. 1 shows an exemplary schematic view of a channel including a chamber zone.

DESCRIPTION OF EMBODIMENTS

The first aspect of the present invention is a method for surface-modifying an object made of a thermoplastic resin, which includes: step 1 of forming polymerization initiation points on the surface of the object; and step 2 of radically polymerizing at least a hydrophilic monomer starting from the polymerization initiation points by irradiation with UV light having a wavelength of 300 to 400 nm to form a graft layer having a thickness of 2 to 100 nm on the surface of the object.

In step 1, polymerization initiation points are formed on the surface of a formed thermoplastic resin (an object to be modified). For example, step 1 may be carried out, for example, by adsorbing a photopolymerization initiator to the surface of the object to form polymerization initiation points, or by adsorbing a photopolymerization initiator to the surface of the object and then irradiating the surface with UV light having a wavelength of 300 to 400 nm to form polymerization initiation points from the photopolymerization initiator on the surface.

Examples of the thermoplastic resin used as the object to be modified include acrylic resins (polyacrylic resins) such as polymethyl acrylate, polymethyl methacrylate, polyacrylic acid, and polymethacrylic acid, cycloolefin resin (polycycloolefin), carbonate resin (polycarbonate), styrene resin (polystyrene), polyester resins such as polyethylene terephthalate (PET), and polydimethylsiloxane.

Examples of the photopolymerization initiator include carbonyl compounds, organic sulfur compounds such as tetraethylthiuram disulfide, persulfides, redox compounds, azo compounds, diazo compounds, halogen compounds, and photoreducing dyes. Preferred among these are carbonyl compounds.

Preferred carbonyl compounds serving as photopolymerization initiators are benzophenone and derivatives thereof (benzophenone compounds). For example, suitable are benzophenone compounds represented by the following formula:

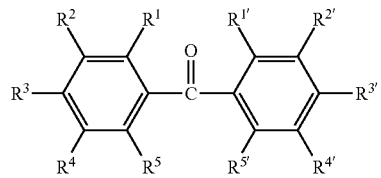

wherein $R^1$ to $R^5$ and $R^{1'}$ to $R^{5'}$ are the same as or different from each other and each represent a hydrogen atom, an alkyl group, halogen (fluorine, chlorine, bromine, or iodine), a hydroxy group, a primary, secondary, or tertiary amino group, a mercapto group, or a hydrocarbon group optionally containing an oxygen, nitrogen, or sulfur atom, and any two adjacent groups of $R^1$ to $R^5$ and $R^{1'}$ to $R^{5'}$ may be joined together to form a ring with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because they contribute to forming polymer brushes well.

The photopolymerization initiator may also suitably be a thioxanthone compound because it provides a high polymerization rate and is easily adsorbed and/or reacted. For example, suitable are compounds represented by the following formula:

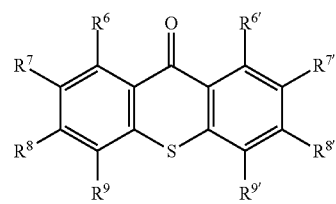

wherein $R^6$ to $R^9$ and $R^{6'}$ to $R^{9'}$ are the same as or different from each other and each represent a hydrogen atom, a halogen atom, or an alkyl, cycloalkyl, aryl, alkenyl, alkoxy, or aryloxy group.

Examples of the thioxanthone compound represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are those which are substituted at one or two, especially two, of $R^6$ to $R^9$ and $R^{6'}$ to $R^{9'}$ with alkyl groups. More preferred is 2,4-diethylthioxanthone.

The adsorption of the photopolymerization initiator such as a benzophenone or thioxanthone compound to the surface of the object may be carried out as follows. In the case of a benzophenone or thioxanthone compound, for example, the benzophenone or thioxanthone compound is dissolved in an organic solvent to prepare a solution; a surface portion of the object to be modified is treated with this solution so that the compound is adsorbed to the surface; and, if necessary, the organic solvent is dried and evaporated, whereby polymerization initiation points are formed. The surface-treating method may be any method that allows the solution of the benzophenone or thioxanthone compound to be brought into contact with the surface of the object. Suitable methods include, for example, application or spraying of the benzophenone or thioxanthone compound solution; or immersion into the solution. Moreover, if only part of the surface needs to be modified, it is sufficient to adsorb the photopolymerization initiator only to the necessary part of the surface. In this case, for example, application or spraying of the solution is suitable. Examples of the solvent include methanol, ethanol, acetone, benzene, toluene, methyl ethyl ketone, ethyl acetate, and THF. Acetone is preferred because it does not swell the object intended to be modified, and it dries and evaporates quickly.

As described above, after the photopolymerization initiator is adsorbed to the surface of the object, the surface may then be irradiated with UV light having a wavelength of 300 to 400 nm to form polymerization initiation points from the photopolymerization initiator on the surface. This UV irradiation may be carried out by known methods, for example, as described below for the UV irradiation in step 2.

In step 2, at least a hydrophilic monomer is radically polymerized starting from the polymerization initiation points formed in step 1, by irradiation with UV light having a wavelength of 300 to 400 nm to form a graft layer (or grow polymer chains) having a thickness of 2 to 100 nm on the surface of the object.

The hydrophilic monomer may be any of various monomers containing hydrophilic groups. Examples of the hydrophilic group include known hydrophilic groups such as an amide group, a sulfuric acid group, a sulfonic acid group, a carboxylic acid group, a hydroxy group, an amino group, and an oxyethylene group.

Specific examples of the hydrophilic monomer include (meth)acrylic acid, (meth)acrylic acid esters (alkoxyalkyl (meth)acrylates such as methoxyethyl (meth)acrylate, and hydroxyalkyl (meth)acrylates such as hydroxyethyl (meth)acrylate)), (meth)acrylamide, and (meth)acrylamide derivatives containing cyclic groups (e.g. (meth)acryloylmorpholine). Preferred among these are (meth)acrylic acid, (meth)acrylic acid esters, and (meth)acryloylmorpholine. More preferred are alkoxyalkyl (meth)acrylates, with 2-methoxyethyl acrylate being particularly preferred.

In step 2, a second monomer other than the hydrophilic monomer may be copolymerized as long as it does not inhibit the effect of the hydrophilic monomer. Examples of the second monomer include aromatic monomers such as styrene, vinyl acetate, and N-isopropylacrylamide which can impart temperature responsiveness.

The radical polymerization of the hydrophilic monomer in step 2 may be carried out, for example, by: (1) applying (spraying) a solution of the hydrophilic monomer onto the surface (outer surface and/or inner surface) of the object on which a benzophenone or thioxanthone compound, for example, has been adsorbed, followed by irradiation with UV light; (2) immersing the object in a solution of the hydrophilic monomer, followed by irradiation with UV light; or (3) injecting a solution of the hydrophilic monomer into the inside of the object (in the shape of, for example, a tube or a channel), followed by irradiation with UV light, whereby radical polymerization (photoradical polymerization) is allowed to proceed to form a graft layer on the surface (outer surface and/or inner surface) of the object. After the application (spraying), immersion, or injection, the surface may further be covered with a transparent cover of glass, PET, polycarbonate or other materials, followed by irradiation with UV light through the transparent cover to allow radical polymerization (photoradical polymerization) to proceed, whereby polymer chains are grown on the surface of the object.

The solvent for application (spraying), the method for application (spraying), the method for immersion, the method for injection, the conditions for irradiation, and other conditions may be conventionally known materials or methods. The solution of the hydrophilic monomer may be, for example, an aqueous solution of a radically polymerizable monomer, or a solution of a radically polymerizable monomer in an organic solvent that does not dissolve the photopolymerization initiator used (e.g. a benzophenone or thioxanthone compound). Moreover, the solution of the hydrophilic monomer may contain a known polymerization inhibitor such as 4-methylphenol.

In the present invention, the radical polymerization of the hydrophilic monomer is allowed to proceed by light irradiation after the application or injection of or immersion in the hydrophilic monomer solution. In the light irradiation, UV light sources with an emission wavelength mainly in the ultraviolet region, such as high-pressure mercury lamps, metal halide lamps, and LED lamps, can be suitably used. The light dose may be selected appropriately in view of polymerization time and uniform progress of the reaction. Moreover, in order to prevent inhibition of polymerization due to active gas such as oxygen in the reaction vessel and the reaction pipe, oxygen is preferably removed from the reaction vessel, the reaction pipe, and the reaction solution (hydrophilic monomer solution) during or before the light irradiation. To this end, appropriate operations may be performed; for example, an inert gas such as nitrogen gas or argon gas is introduced into the reaction vessel or pipe and the reaction solution to discharge active gas such as oxygen from the reaction system and replace the atmosphere in the reaction system with the inert gas. Furthermore, in order to prevent inhibition of the reaction due to oxygen and other gases, for example, a measure may also appropriately be taken in which an UV light source is placed such that an air layer (oxygen content: 15% or higher) does not exist between the reaction vessel made of glass, plastic, or other materials and the reaction solution or the object intended to be modified.

The UV light used has a wavelength of 300 to 400 nm. Such a wavelength enables polymer chains (a graft layer) to be formed well on the surface of the object to be modified. Examples of light sources that can be used include high-pressure mercury lamps, LEDs with a center wavelength of 365 nm, and LEDs with a center wavelength of 375 nm. More preferred is irradiation with LED light having a wavelength of 355 to 380 nm. In particular, for example, LEDs with a center wavelength of 365 nm, which is close to the excitation wavelength (366 nm) of benzophenone, are preferred in view of efficiency. Light having a wavelength of shorter than 300 nm can cleave and damage molecules of the object. For this reason, light having a wavelength of 300 nm or longer is preferred. More preferred is light having a wavelength of 355 nm or longer because it produces very little damage to the object. However, light having a wavelength of longer than 400 nm is less likely to activate the photopolymerization initiator, so that the polymerization reaction does not readily proceed. For this reason, light having a wavelength of 400 nm or shorter is preferred. Although LED light is suitable because the wavelength range of LED light is narrow so that no wavelengths other than the center wavelength are emitted, mercury lamps or other light sources can also achieve similar effects to those of LED light if a filter is used to block light with wavelengths shorter than 300 nm.

The second aspect of the present invention is a method for surface-modifying an object made of a thermoplastic resin, which includes step I of radically polymerizing at least a hydrophilic monomer by irradiation with UV light having a wavelength of 300 to 400 nm in the presence of a photopolymerization initiator to form a graft layer having a thickness of 2 to 100 nm on the surface of the object. Specifically, a hydrophilic monomer is radically polymerized by irradiation with UV light in the presence of a photopolymerization initiator used as the initiator to form polymer chains (a graft layer), whereby a surface-modified body can be produced in which a graft layer formed of hydrophilic polymer chains is provided on the surface of an object to be modified. The object to be modified, the photopolymerization initiator, and the hydrophilic monomer used in step I may be as described hereinabove.

For example, step I may be carried out by contacting the surface of the object with the photopolymerization initiator and the hydrophilic monomer, and then irradiating the surface with LED light having a wavelength of 300 to 400 nm to form polymerization initiation points from the photopolymerization initiator while radically polymerizing the hydrophilic monomer starting from the polymerization initiation points to grow polymer chains (or form a graft layer).

The radical polymerization of the hydrophilic monomer in step I may be carried out, for example, by: (1) applying (spraying) a solution of the hydrophilic monomer containing the photopolymerization initiator (e.g. a benzophenone or thioxanthone compound) onto the surface of the object, followed by irradiation with UV light; (2) immersing the object in a solution of the hydrophilic monomer containing the photopolymerization initiator, followed by irradiation with UV light; or (3) injecting a solution of the hydrophilic monomer containing the photopolymerization initiator into the inside of the object (in the shape of, for example, a tube or a channel), followed by irradiation with UV light, whereby radical polymerization (photoradical polymerization) is allowed to proceed to form a graft layer on the surface (outer surface and/or inner surface) of the object. Further, for example, the surface may be covered with a transparent cover of glass, PET, polycarbonate, or other materials, followed by irradiation with UV light through the transparent cover as described hereinabove. The solvent for application (spraying), the method for application (spraying), the method for immersion, the method for injection, the conditions for irradiation, and other conditions may be the materials or methods described hereinabove.

The graft layer formed in step 2 or step I (the graft layer formed of hydrophilic polymer chains) has a thickness of 2 to 100 nm, preferably 2 to 50 nm, more preferably 2 to 30 nm. If the thickness is less than 2 nm, low adsorption of proteins and cells and selective adsorption or adhesion of cancer cells tend not to be well achieved. If the thickness is more than 100 nm, low adsorption of proteins and cells and selective adsorption or adhesion of cancer cells tend to deteriorate.

The duration of UV irradiation in step 2 or step I is preferably 15 to 250 minutes, more preferably 30 to 200 minutes, still more preferably 30 to 150 minutes. When the duration is less than 15 minutes, low adsorption of proteins and cells and selective adsorption or adhesion of cancer cells tend not to be well achieved. When the duration is more than 250 minutes, low adsorption of proteins and cells and selective adsorption or adhesion of cancer cells tend to deteriorate.

In step 2 or step I, two or more types of monomers may be radically polymerized simultaneously. Moreover, multiple types of polymer chains may be grown on the surface of the object. In the surface modification methods of the present invention, the polymer chains may be cross-linked to each other. In this case, the polymer chains may be cross-linked to each other by ionic crosslinking, crosslinking by a hydrophilic group containing an oxygen atom, or crosslinking by a halogen group such as iodine.

The surface modification methods can be applied to thermoplastic resins to produce surface-modified bodies at least part of whose surface is modified. Specifically, matrices (e.g. substrates, chips, instruments for testing), filters, channels, tubes, and other devices for medical and healthcare use can be produced. The modification may preferably be applied to at least a surface portion to be in contact with blood or biological fluid of a device for medical and healthcare use, such as a matrix (e.g. a matrix for collecting and adsorbing a specific protein or specific cells, such as cancer cells, from a blood sample or a biological fluid sample), filter, channel, or tube. The entire surface may be modified. By appropriately selecting the type of hydrophilic monomer according to the desired properties, proteins and cells in blood or biological fluid can be prevented from adhering or adsorbing to the surface, and the surface can selectively adhere or adsorb to specific cells such as cancer cells. In addition, excellent durability is also obtained because the polymer chains are fixed to the surface such that, for example, they do not peel off even when the surface is washed or treated with chemicals.

EXAMPLES

The present invention is described in greater detail below with reference to examples, but is not limited only thereto.

Example 1

A 3% by mass solution of benzophenone in acetone was applied to the surface of a polyethylene terephthalate (PET) object intended to be modified, so that benzophenone was adsorbed to the surface, followed by drying.

Subsequently, the surface was immersed in a 10% by mass solution of 2-methoxyethyl acrylate in a mixture of water and ethanol (water:ethanol=1:1) in a glass reaction vessel. The reaction vessel was sealed with a rubber stopper, and argon gas was introduced and allowed to bubble through the solution for 120 minutes to remove oxygen. While being rotated, the glass reaction vessel was irradiated with LED light having a wavelength of 365 nm for 60 minutes to cause radical polymerization, whereby a graft layer was grown on the PET surface. Thus, a surface-modified body was prepared.

Example 2

A surface-modified body was prepared as in Example 1, except that the duration of LED light irradiation was changed to 30 minutes.

Example 3

A surface-modified body was prepared as in Example 1, except that the duration of LED light irradiation was changed to 120 minutes.

Example 4

A surface-modified body was prepared as in Example 1, except that the duration of LED light irradiation was changed to 180 minutes.

Example 5

A surface-modified body was prepared as in Example 1, except that polycycloolefin was used instead of PET.

Example 6

A surface-modified body was prepared as in Example 1, except that polymethyl methacrylate was used instead of PET.

Example 7

A 3% by mass solution of benzophenone in acetone was injected into a channel made of polycycloolefin provided with a chamber zone as shown in FIG. 1, so that benzophenone was adsorbed, and then the acetone solution was discharged, followed by drying.

Subsequently, a 10% by mass solution of 2-methoxyethyl acrylate in a mixture of water and ethanol (water:ethanol=1:1), from which oxygen was previously removed by bubbling with argon gas, was injected to the channel, followed by irradiation with LED light having a wavelength of 365 nm for 60 minutes to cause radical polymerization, whereby a graft layer was grown on the polycycloolefin surface (chamber inner surface). Thus, a surface-modified body was prepared.

Example 8

A surface-modified body was prepared as in Example 7, except that the channel made of polycycloolefin was replaced with a similar channel provided with a chamber zone, but made of polymethyl methacrylate.

Comparative Example 1

Untreated PET was used.

Comparative Example 2

A surface-modified body was prepared as in Example 1, except that the duration of LED light irradiation was changed to 300 minutes.

The surface-modified bodies prepared in the examples and comparative examples were evaluated as follows.

(Thickness of Graft Layer)

The thickness of the graft layer on the surface of the surface-modified body was determined by measuring (photographing) the cross-section of the surface-modified body on which the graft layer (hydrophilic polymer chains) was formed using a TEM at an accelerating voltage of 15 kV and a magnification of ×1000.

(Amount of Platelets Adsorbed)

A liquid prepared by mixing plasma and platelets to adjust the concentration of platelets (plating density) to $4\times10^7$ cells/cm² was brought into contact with the surface of a sample (surface-modified body), and then the sample was allowed to stand at 37° C. for one hour. The surface of the sample was washed with phosphate-buffered saline, followed by fixation using 1% glutaraldehyde (standing at 37° C. for two hours). Thereafter, the surface of the sample was again washed with phosphate-buffered saline and distilled water.

This sample was observed by SEM, and the number of platelets adsorbed was counted. The number of platelets is expressed as a value relative to that of Comparative Example 1 which is taken as 1.

(Amount of Cancer Cells Adhered)

A suspension of human fibrosarcoma (HT1080: a type of cancer cell) (FBS, plating density: $1\times10^4$ cells/cm²) was brought into contact with the surface of a sample (surface-modified body), and then the sample was allowed to stand at 37° C. for one hour. The surface of the sample was washed with phosphate-buffered saline, followed by fixation using 1% glutaraldehyde (standing at 37° C. for two hours). Thereafter, the surface of the sample was again washed with phosphate-buffered saline and distilled water.

This sample was observed by SEM, and the number of cancer cells adhered was counted. The number of cancer cells is expressed as a value relative to that of Comparative Example 1 which is taken as 1.

TABLE 1

|  | Example | | | | | | | |
| --- | --- | --- | --- | --- | --- | --- | --- | --- |
|  | 1 | 2 | 3 | 4 | 5 | 6 | 7 | 8 |
| Thickness of graft layer (nm) | 4.94 | 2.52 | 28.4 | 68.3 | 3.26 | 4.85 | 2.86 | 4.51 |
| Amount of platelets adsorbed | 0.01 | 0.02 | 0.03 | 0.04 | 0.02 | 0.01 | 0.02 | 0.02 |
| Amount of cancer cells adhered | 0.73 | 0.71 | 0.62 | 0.47 | 0.56 | 0.65 | 0.52 | 0.66 |
| Selectivity | 73.0 | 35.5 | 20.7 | 11.8 | 28.0 | 65.0 | 26.0 | 33.0 |

|  | Comparative Example | |
| --- | --- | --- |
|  | 1 | 2 |
| Thickness of graft layer (nm) | — | 112 |
| Amount of platelets adsorbed | 1 | 0.09 |
| Amount of cancer cells adhered | 1 | 0.31 |
| Selectivity | 1.0 | 3.4 |

Selectivity = Amount of cancer cells adhered/Amount of platelets adsorbed

With the surface-modified bodies of the examples each having a graft layer with a specific thickness, a small amount of platelets were adsorbed while a large amount of cancer cells were adhered, and good selectivity (amount of cancer cells adhered/amount of platelets adsorbed) exceeding 10 was also obtained. In contrast, in Comparative Example 1 using the untreated PET surface, a large amount of cancer cells were adhered but a large amount of platelets were also adsorbed, and thus the selectivity was low. The surface-modified body of Comparative Example 2 having a thicker graft layer was greatly inferior in selectivity to the examples because the amount of platelets adsorbed was slightly large and the amount of cancer cells adhered was slightly small. These results demonstrated that the properties of low platelet adsorption and the properties of high cancer cell adhesion highly depend on the thickness of the graft layer (the length of the polymer chain), and too large a thickness leads to greatly reduced selectivity.

Accordingly, by adjusting the thickness of the graft layer within the specific range of 2 to 100 nm, selectivity is improved so that properties such as selective capture of cancer cells from blood can be expected to be provided.

REFERENCE SIGNS LIST

1: Medical testing device
11: Channel
12: Chamber zone

The invention claimed is:

1. A method for adhering or adsorbing cancer cells to a thermoplastic resin surface, the method comprising:

step (1) of forming polymerization initiation points on the thermoplastic resin surface; and step (2) of radically polymerizing at least a hydrophilic monomer starting from the polymerization initiation points by irradiation with UV light having a wavelength of 300 to 400 nm to form a graft layer having a thickness of 2 to 100 nm on at least a portion of the thermoplastic resin surface to form a modified surface, step (3) of exposing the modified surface to blood or biological fluid in order to adhere or adsorb cancer cells in the blood or the biological fluid to the modified surface, wherein
the hydrophilic monomer is an alkoxyalkyl acrylate, and
the thermoplastic resin surface forms at least a part of at least one member selected from the group consisting of a matrix, filter, channel, and tube.

2. A method for adhering or adsorbing cancer cells to a thermoplastic resin surface, the method comprising
step (I) of radically polymerizing at least a hydrophilic monomer by irradiation with UV light having a wavelength of 300 to 400 nm in the presence of a photopolymerization initiator to form a graft layer having a thickness of 2 to 100 nm on at least a portion of the thermoplastic resin surface to produce a modified surface,
step (II) of exposing the modified surface to biological fluids in order to adhere or adsorb cancer cells in the blood or the biological fluid to the modified surface,
wherein the hydrophilic monomer is an alkoxyalkyl acrylate, and
the thermoplastic resin surface forms at least a part of at least one member selected from the group consisting of a matrix, filter, channel, and tube.

3. The method according to claim 1, wherein step (1) comprises adsorbing a photopolymerization initiator to the thermoplastic resin surface, optionally followed by irradiation with UV light having a wavelength of 300 to 400 nm, to form polymerization initiation points from the photopolymerization initiator on the surface.

4. The method according to claim 3, wherein the photopolymerization initiator is at least one of a benzophenone compound or a thioxanthone compound.

5. The method according to claim 1, wherein an inert gas is introduced into a reaction vessel or pipe containing a solution of the hydrophilic monomer so that the monomer is radically polymerized in an atmosphere replaced with the inert gas.

6. The method according to claim 1, wherein a solution of the hydrophilic monomer containing a polymerization inhibitor is used, and the monomer is radically polymerized in the presence of the polymerization inhibitor.

7. The method according to claim 1, wherein the thermoplastic resin is at least one selected from the group consisting of acrylic resins, cycloolefin resin, carbonate resin, styrene resin, and polyester resins.

8. The method according to claim 3, wherein an inert gas is introduced into a reaction vessel or pipe containing a solution of the hydrophilic monomer so that the monomer is radically polymerized in an atmosphere replaced with the inert gas.

9. The method according to claim 3, wherein a solution of the hydrophilic monomer containing a polymerization inhibitor is used, and the monomer is radically polymerized in the presence of the polymerization inhibitor.

10. The method according to claim 3, wherein the thermoplastic resin is at least one selected from the group consisting of acrylic resins, cycloolefin resin, carbonate resin, styrene resin, and polyester resins.

11. The method according to claim 1, wherein the thermoplastic resin is at least one selected from the group consisting of polymethyl acrylate, polymethyl methacrylate, polyacrylic acid, polymethacrylic acid, polycycloolefin, and polyethylene terephthalate.

12. The method according to claim 2, wherein the thermoplastic resin is at least one selected from the group consisting of polymethyl acrylate, polymethyl methacrylate, polyacrylic acid, polymethacrylic acid, polycycloolefin, and polyethylene terephthalate.

13. The method according to claim 1, wherein at least an alkoxyalkyl acrylate and N-isopropylacrylamide as hydrophilic monomers are radically polymerized in step (2) starting from the polymerization initiation points by irradiation with UV light having a wavelength of 300 to 400 nm to form a graft layer having a thickness of 2 to 100 nm.

14. The method according to claim 2, wherein at least an alkoxyalkyl acrylate and N-isopropylacrylamide as hydrophilic monomers are radically polymerized in step (I) starting from the polymerization initiation points by irradiation with UV light having a wavelength of 300 to 400 nm to form a graft layer having a thickness of 2 to 100 nm.

\* \* \* \* \*